(12) United States Patent
Goitsuka

(10) Patent No.: US 6,831,151 B1
(45) Date of Patent: Dec. 14, 2004

(54) MAST CELL-SPECIFIC SIGNAL TRANSDUCING MOLECULES AND CDNAS THEREOF

(75) Inventor: Ryo Goitsuka, Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 140 days.

(21) Appl. No.: 09/856,061

(22) PCT Filed: Sep. 18, 2000

(86) PCT No.: PCT/JP00/06351

§ 371 (c)(1),
(2), (4) Date: Jul. 10, 2001

(87) PCT Pub. No.: WO01/21788

PCT Pub. Date: Mar. 29, 2001

(30) Foreign Application Priority Data

Sep. 17, 1999 (JP) .......................................... 11-263778

(51) Int. Cl.[7] .............................................. C07K 14/47
(52) U.S. Cl. ..................................................... 530/350
(58) Field of Search .......................................... 530/350

(56) References Cited

PUBLICATIONS

Goitsuka et al. Int. Immunol. 12: 573–580 (2000).*
Cao et al., J. Exp. Med., vol. 190, No. 10, pp. 1527–1534 (1999).
Goitsuka et al., J. Immunol., vol. 161, pp. 5804–5808 (1998).
Jackman et al., J. Biol. Chem., vol. 270, No. 13, pp. 7029–7032 (1995).

* cited by examiner

*Primary Examiner*—Robert A. Wax
(74) *Attorney, Agent, or Firm*—Wenderoth, Lind & Ponack, L.L.P.

(57) ABSTRACT

The present invention provides a signal transducer specifically expressed in mouse mast cells that has the amino acid sequence of SEQ ID No. 2, a signal transducer specifically expressed in human mast cells that has the amino acid sequence of SEQ ID No. 4, polynucleotides encoding these proteins, an expression vector involving these polynucleotides, transformed cells induced by these expression vectors, and antibodies against the foregoing proteins. The signal transducer provided in the present invention is useful for screening of novel medicines against allergic diseases.

2 Claims, 3 Drawing Sheets

SEQUENCE LISTING

```
<160> NUMBER OF SEQ ID NOS: 4

<210> SEQ ID NO 1
<211> LENGTH: 1721
<212> TYPE: DNA
<213> ORGANISM: Mus musculus
<220> FEATURE:
<221> NAME/KEY: CDS
<222> LOCATION: (255)..(1562)
<300> PUBLICATION INFORMATION:
<301> AUTHORS: Goitsuka R., et al.
<302> TITLE: A BASH/SLP-76-related adaptor protein MIST/Clink involved
      in IgE receptor-mediated mast cell degranuation
<303> JOURNAL: Int. Immunol.
<304> VOLUME: 12
<305> ISSUE: 4
<306> PAGES: 573-580
<307> DATE: 2000-05-26
<308> DATABASE ACCESSION NUMBER: GenBank/AB021220
<309> DATABASE ENTRY DATE: 2000-05-26

<400> SEQUENCE: 1
acgaggccaa actgcccagg tctgtggctg cgtttctcgg aaaaccaaaa ctcaacaggc      60
acatacaagg cactctctgc tgaaggactc tgctgagggg agagaacatg tcaactctat     120
cttacagagt gctccaggat gcgaccgtgg accccctttc caggagctag ccgtctcaac     180
actgagccct tgactaaagg aagactgagc aggctgagtt gaagatccct ctcttttgcc     240
aggtgccaag gacc atg acc agc cag ggc aat aaa agg aca acg aaa gaa       290
             Met Thr Ser Gln Gly Asn Lys Arg Thr Thr Lys Glu
              1               5                  10 gga ttc ggt gat ctg aga ttc cag aac gtc tct ctg ctg aaa aat agg       338
Gly Phe Gly Asp Leu Arg Phe Gln Asn Val Ser Leu Leu Lys Asn Arg
         15                  20                  25 tca tgg cca agc ctc agc agt gcc aaa ggg cgg tgt cga gcg gtt ctg       386
Ser Trp Pro Ser Leu Ser Ser Ala Lys Gly Arg Cys Arg Ala Val Leu
     30                  35                  40 gaa cca ctt ccg gat cac aga agg aac ttg gct ggg gtc cca ggt gga       434
Glu Pro Leu Pro Asp His Arg Arg Asn Leu Ala Gly Val Pro Gly Gly
 45                  50                  55                  60 gaa aaa tgc aac agt aac aac gac tac gaa gat cct gag ttc cag ctg       482
Glu Lys Cys Asn Ser Asn Asn Asp Tyr Glu Asp Pro Glu Phe Gln Leu
                 65                  70                  75 ctg aag gca tgg cca tca atg aaa att tta cca gcc aga cct atc cag       530
Leu Lys Ala Trp Pro Ser Met Lys Ile Leu Pro Ala Arg Pro Ile Gln
             80                  85                  90 gaa tcg gaa tac gca gat aca cgc tat ttc cag gat atg atg gag gct       578
Glu Ser Glu Tyr Ala Asp Thr Arg Tyr Phe Gln Asp Met Met Glu Ala
         95                  100                 105
```

-continued

| | |
|---|---|
| ccc ctt ctg tta cct ccc aag gct tct gtc tcc act gag aga caa acc<br>Pro Leu Leu Leu Pro Pro Lys Ala Ser Val Ser Thr Glu Arg Gln Thr<br>110                    115                    120 | 626 |
| agg gat gtg agg atg aca cag ctg gaa gaa gtg gac aag cct acc ttc<br>Arg Asp Val Arg Met Thr Gln Leu Glu Glu Val Asp Lys Pro Thr Phe<br>125                    130                    135                    140 | 674 |
| aag gat gtc aga agc caa cgc ttt aaa gga ttc aaa tac aca aaa ata<br>Lys Asp Val Arg Ser Gln Arg Phe Lys Gly Phe Lys Tyr Thr Lys Ile<br>                    145                    150                    155 | 722 |
| aac aag act cct ttg cca cct cct cgg cct gct atc act ctc ccc aag<br>Asn Lys Thr Pro Leu Pro Pro Pro Arg Pro Ala Ile Thr Leu Pro Lys<br>                160                    165                    170 | 770 |
| aag tac caa ccc tta ccc cca gca cca cca gag gag agc agt gca tac<br>Lys Tyr Gln Pro Leu Pro Pro Ala Pro Pro Glu Glu Ser Ser Ala Tyr<br>                    175                    180                    185 | 818 |
| ttc gct cca aag ccc acc ttt cca gaa gtc cag agg ggg ccc agg cag<br>Phe Ala Pro Lys Pro Thr Phe Pro Glu Val Gln Arg Gly Pro Arg Gln<br>190                    195                    200 | 866 |
| agg agt gca aaa gac ttc agt agg gtc ctt gga gca gaa gaa gaa tct<br>Arg Ser Ala Lys Asp Phe Ser Arg Val Leu Gly Ala Glu Glu Glu Ser<br>205                    210                    215                    220 | 914 |
| cac cac cag aca aag cca gaa tct tct tgc cca tca tca aac caa aac<br>His His Gln Thr Lys Pro Glu Ser Ser Cys Pro Ser Ser Asn Gln Asn<br>                    225                    230                    235 | 962 |
| aca cag aag agt cca cct gcc att gcc agc tct tcc tac atg cca gga<br>Thr Gln Lys Ser Pro Pro Ala Ile Ala Ser Ser Ser Tyr Met Pro Gly<br>                    240                    245                    250 | 1010 |
| aag cac agt ata caa gcc aga gac cat aca ggt agc atg cag cac tgt<br>Lys His Ser Ile Gln Ala Arg Asp His Thr Gly Ser Met Gln His Cys<br>                    255                    260                    265 | 1058 |
| cct gct cag aga tgc caa gct gca gcc agc cac agc cct cga atg ctg<br>Pro Ala Gln Arg Cys Gln Ala Ala Ala Ser His Ser Pro Arg Met Leu<br>270                    275                    280 | 1106 |
| ccc tat gaa aac aca aac tcg gag aaa cct gac ccc aca aag cct gat<br>Pro Tyr Glu Asn Thr Asn Ser Glu Lys Pro Asp Pro Thr Lys Pro Asp<br>285                    290                    295                    300 | 1154 |
| gag aag gat gtc tgg cag aat gaa tgg tac att gga gaa tac agt cgc<br>Glu Lys Asp Val Trp Gln Asn Glu Trp Tyr Ile Gly Glu Tyr Ser Arg<br>                    305                    310                    315 | 1202 |
| cag gca gtg gaa gat gtg tta atg aaa gag aac aag gat ggt act ttt<br>Gln Ala Val Glu Asp Val Leu Met Lys Glu Asn Lys Asp Gly Thr Phe<br>320                    325                    330 | 1250 |
| ttg gtc cga gac tgc tct aca aaa tcc aag gca gaa cca tat gtt ttg<br>Leu Val Arg Asp Cys Ser Thr Lys Ser Lys Ala Glu Pro Tyr Val Leu<br>                    335                    340                    345 | 1298 |
| gtg gtg ttt tat ggg aac aag gtc tac aat gtg aaa atc cgt ttc ctc<br>Val Val Phe Tyr Gly Asn Lys Val Tyr Asn Val Lys Ile Arg Phe Leu<br>350                    355                    360 | 1346 |
| gag agc aat caa cag ttt gcc ctg ggc aca gga cta cga gga aat gag<br>Glu Ser Asn Gln Gln Phe Ala Leu Gly Thr Gly Leu Arg Gly Asn Glu<br>365                    370                    375                    380 | 1394 |
| atg ttt gat tct gtg gaa gac atc att gaa cac tac aca tat ttt ccc<br>Met Phe Asp Ser Val Glu Asp Ile Ile Glu His Tyr Thr Tyr Phe Pro<br>                    385                    390                    395 | 1442 |
| att ctg cta ata gat ggg aaa gac aag gct gca cgc agg aaa cag tgc<br>Ile Leu Leu Ile Asp Gly Lys Asp Lys Ala Ala Arg Arg Lys Gln Cys<br>                    400                    405                    410 | 1490 |
| tac ctc acc cag cca ctg cct ctc gcc agg ctc ctt ctc act cag tac<br>Tyr Leu Thr Gln Pro Leu Pro Leu Ala Arg Leu Leu Leu Thr Gln Tyr | 1538 |

-continued

```
                   415                 420                 425
tcc agc cag gca ctt cat gag taa gaagcccagc cagatatccc cgcatcagtg      1592
Ser Ser Gln Ala Leu His Glu
        430                 435 gcctgggcct tgtctcattc ctggctcaat ggattcagtt cttcttccat ctgcatttat      1652
ctgcaaagta ttattttctg tgtcttcaag ggatgatttt ttgactctgt aaaaaaaaaa      1712
aaaaaaaaa                                                              1721
```

<210> SEQ ID NO 2
<211> LENGTH: 435
<212> TYPE: PRT
<213> ORGANISM: Mus musculus

<400> SEQUENCE: 2

```
Met Thr Ser Gln Gly Asn Lys Arg Thr Thr Lys Glu Gly Phe Gly Asp
 1               5                  10                  15

Leu Arg Phe Gln Asn Val Ser Leu Leu Lys Asn Arg Ser Trp Pro Ser
            20                  25                  30

Leu Ser Ser Ala Lys Gly Arg Cys Arg Ala Val Leu Glu Pro Leu Pro
        35                  40                  45

Asp His Arg Arg Asn Leu Ala Gly Val Pro Gly Gly Glu Lys Cys Asn
    50                  55                  60

Ser Asn Asn Asp Tyr Glu Asp Pro Glu Phe Gln Leu Leu Lys Ala Trp
65                  70                  75                  80

Pro Ser Met Lys Ile Leu Pro Ala Arg Pro Ile Gln Glu Ser Glu Tyr
                85                  90                  95

Ala Asp Thr Arg Tyr Phe Gln Asp Met Met Glu Ala Pro Leu Leu Leu
            100                 105                 110

Pro Pro Lys Ala Ser Val Ser Thr Glu Arg Gln Thr Arg Asp Val Arg
        115                 120                 125

Met Thr Gln Leu Glu Glu Val Asp Lys Pro Thr Phe Lys Asp Val Arg
    130                 135                 140

Ser Gln Arg Phe Lys Gly Phe Lys Tyr Thr Lys Ile Asn Lys Thr Pro
145                 150                 155                 160

Leu Pro Pro Pro Arg Pro Ala Ile Thr Leu Pro Lys Lys Tyr Gln Pro
                165                 170                 175

Leu Pro Pro Ala Pro Pro Glu Glu Ser Ser Ala Tyr Phe Ala Pro Lys
            180                 185                 190

Pro Thr Phe Pro Glu Val Gln Arg Gly Pro Arg Gln Arg Ser Ala Lys
        195                 200                 205

Asp Phe Ser Arg Val Leu Gly Ala Glu Glu Ser His His Gln Thr
    210                 215                 220

Lys Pro Glu Ser Ser Cys Pro Ser Ser Asn Gln Asn Thr Gln Lys Ser
225                 230                 235                 240

Pro Pro Ala Ile Ala Ser Ser Tyr Met Pro Gly Lys His Ser Ile
                245                 250                 255

Gln Ala Arg Asp His Thr Gly Ser Met Gln His Cys Pro Ala Gln Arg
            260                 265                 270

Cys Gln Ala Ala Ala Ser His Ser Pro Arg Met Leu Pro Tyr Glu Asn
        275                 280                 285

Thr Asn Ser Glu Lys Pro Asp Pro Thr Lys Pro Asp Glu Lys Asp Val
    290                 295                 300

Trp Gln Asn Glu Trp Tyr Ile Gly Glu Tyr Ser Arg Gln Ala Val Glu
305                 310                 315                 320
```

```
Asp Val Leu Met Lys Glu Asn Lys Asp Gly Thr Phe Leu Val Arg Asp
                325                 330                 335

Cys Ser Thr Lys Ser Lys Ala Glu Pro Tyr Val Leu Val Phe Tyr
            340                 345                 350

Gly Asn Lys Val Tyr Asn Val Lys Ile Arg Phe Leu Glu Ser Asn Gln
            355                 360                 365

Gln Phe Ala Leu Gly Thr Gly Leu Arg Gly Asn Glu Met Phe Asp Ser
        370                 375                 380

Val Glu Asp Ile Ile Glu His Tyr Thr Tyr Phe Pro Ile Leu Leu Ile
385                 390                 395                 400

Asp Gly Lys Asp Lys Ala Ala Arg Arg Lys Gln Cys Tyr Leu Thr Gln
                405                 410                 415

Pro Leu Pro Leu Ala Arg Leu Leu Thr Gln Tyr Ser Ser Gln Ala
                420                 425                 430

Leu His Glu
        435
```

<210> SEQ ID NO 3
<211> LENGTH: 1129
<212> TYPE: DNA
<213> ORGANISM: Homo sapiens
<220> FEATURE:
<221> NAME/KEY: CDS
<222> LOCATION: (1)..(1128)
<300> PUBLICATION INFORMATION:
<301> AUTHORS: Goitsuka R., et al.
<302> TITLE: A BASH/SLP-76-related adaptor protein MIST/Clink involved in IgE receptor-mediated mast cell degranuation
<303> JOURNAL: Int. Immunol.
<304> VOLUME: 12
<305> ISSUE: 4
<306> PAGES: 573-580
<307> DATE: 2000-05-26
<308> DATABASE ACCESSION NUMBER: GenBank/AB021220
<309> DATABASE ENTRY DATE: 2000-05-26

<400> SEQUENCE: 3

```
ttc cag aac ttc agt ctg cca aaa aac agg tca tgg cct cgc atc aat      48
Phe Gln Asn Phe Ser Leu Pro Lys Asn Arg Ser Trp Pro Arg Ile Asn
 1               5                  10                  15 agt gcc aca ggc cag tac cag agg atg aac aag cct ctt cta gac tgg      96
Ser Ala Thr Gly Gln Tyr Gln Arg Met Asn Lys Pro Leu Leu Asp Trp
             20                  25                  30 gaa aga aac ttt gct gca gtc ctg gat gga gca aaa ggc cac agt gat     144
Glu Arg Asn Phe Ala Ala Val Leu Asp Gly Ala Lys Gly His Ser Asp
         35                  40                  45 gat gac tat gat gac cct gag ctt cgg atg gaa gag aca tgg cag tcg     192
Asp Asp Tyr Asp Asp Pro Glu Leu Arg Met Glu Glu Thr Trp Gln Ser
     50                  55                  60 att aaa att tta cca gcc cgg cct ata aag gaa tct gaa tat gca gat     240
Ile Lys Ile Leu Pro Ala Arg Pro Ile Lys Glu Ser Glu Tyr Ala Asp
 65                  70                  75                  80 aca cac tat ttc aag gtt gca atg gac act ccc ctt ccg tta gac acc     288
Thr His Tyr Phe Lys Val Ala Met Asp Thr Pro Leu Pro Leu Asp Thr
                 85                  90                  95 agg acc tct atc tcc att gga cag ccg acc tgg aac aca cag acg agg     336
Arg Thr Ser Ile Ser Ile Gly Gln Pro Thr Trp Asn Thr Gln Thr Arg
            100                 105                 110 ttg gaa aga gtg gac aaa ccc att tcc agg gac gtc aga agc caa aac     384
Leu Glu Arg Val Asp Lys Pro Ile Ser Arg Asp Val Arg Ser Gln Asn
        115                 120                 125
```

-continued

```
att aaa gga gat gca tcc gta aga aag aac aag att cct tta cca cct      432
Ile Lys Gly Asp Ala Ser Val Arg Lys Asn Lys Ile Pro Leu Pro Pro
    130             135                 140 cct cgg cct ctc ata aca ctt ccg aag aag tac caa ccc ttg ccc cct      480
Pro Arg Pro Leu Ile Thr Leu Pro Lys Lys Tyr Gln Pro Leu Pro Pro
145                 150                 155                 160 gag ccg gag agc agc agg cca cct tta tct cag aga cac acc ttt cca      528
Glu Pro Glu Ser Ser Arg Pro Pro Leu Ser Gln Arg His Thr Phe Pro
                165                 170                 175 gaa gtc cag gga atg ccc agt cag ata agc tta agg gac tta agt gag      576
Glu Val Gln Gly Met Pro Ser Gln Ile Ser Leu Arg Asp Leu Ser Glu
            180                 185                 190 gtc ctt gaa gca gaa aaa gtt cct cat aac cag agg aag cct gaa tca      624
Val Leu Glu Ala Glu Lys Val Pro His Asn Gln Arg Lys Pro Glu Ser
        195                 200                 205 act cat ctg tta gaa aac caa aat act caa gag att cca ctt gcc att      672
Thr His Leu Leu Glu Asn Gln Asn Thr Gln Glu Ile Pro Leu Ala Ile
    210                 215                 220 agc agt tct tca ttc acg aca agc aac cac agt gtg caa aac aga gat      720
Ser Ser Ser Ser Phe Thr Thr Ser Asn His Ser Val Gln Asn Arg Asp
225                 230                 235                 240 cat aga gga ggc atg cag ccc tgt tct cct cag aga tgc cag cct cca      768
His Arg Gly Gly Met Gln Pro Cys Ser Pro Gln Arg Cys Gln Pro Pro
                245                 250                 255 gcc agc tgc agc cct cac gaa aat ata ctg ccc tat aaa tac aca agc      816
Ala Ser Cys Ser Pro His Glu Asn Ile Leu Pro Tyr Lys Tyr Thr Ser
            260                 265                 270 tgg aga cca cct ttc ccc aaa agg tct gat aga aag gat gtc cag cac      864
Trp Arg Pro Pro Phe Pro Lys Arg Ser Asp Arg Lys Asp Val Gln His
        275                 280                 285 aat gaa tgg tac att gga gaa tac agc cgc cag gca gtg gaa gag gca      912
Asn Glu Trp Tyr Ile Gly Glu Tyr Ser Arg Gln Ala Val Glu Glu Ala
    290                 295                 300 ttc atg aag gag aac aag gat ggt agt ttc ttg gtc cga gat tgt tcc      960
Phe Met Lys Glu Asn Lys Asp Gly Ser Phe Leu Val Arg Asp Cys Ser
305                 310                 315                 320 aca aaa tcc aag gaa gag ccc tat gtt ttg gct gtg ttt tat gag aac     1008
Thr Lys Ser Lys Glu Glu Pro Tyr Val Leu Ala Val Phe Tyr Glu Asn
                325                 330                 335 aaa gtc tac aat gta aaa atc cgc ttc ctg gag agg aat cag cag ttt     1056
Lys Val Tyr Asn Val Lys Ile Arg Phe Leu Glu Arg Asn Gln Gln Phe
            340                 345                 350 gcc ctg ggg aca gga ctc aga gga gat gag aag ttt gat tca gta gaa     1104
Ala Leu Gly Thr Gly Leu Arg Gly Asp Glu Lys Phe Asp Ser Val Glu
        355                 360                 365 gac atc atc gaa cac tac aag aat t                                   1129
Asp Ile Ile Glu His Tyr Lys Asn
    370                 375
```

<210> SEQ ID NO 4
<211> LENGTH: 376
<212> TYPE: PRT
<213> ORGANISM: Homo sapiens

<400> SEQUENCE: 4

```
Phe Gln Asn Phe Ser Leu Pro Lys Asn Arg Ser Trp Pro Arg Ile Asn
  1               5                  10                  15

Ser Ala Thr Gly Gln Tyr Gln Arg Met Asn Lys Pro Leu Leu Asp Trp
                20                  25                  30

Glu Arg Asn Phe Ala Ala Val Leu Asp Gly Ala Lys Gly His Ser Asp
```

-continued

```
                    35                    40                    45
Asp Asp Tyr Asp Asp Pro Glu Leu Arg Met Glu Thr Trp Gln Ser
         50                    55                    60

Ile Lys Ile Leu Pro Ala Arg Pro Ile Lys Glu Ser Glu Tyr Ala Asp
 65                    70                    75                    80

Thr His Tyr Phe Lys Val Ala Met Asp Thr Pro Leu Pro Leu Asp Thr
                 85                    90                    95

Arg Thr Ser Ile Ser Ile Gly Gln Pro Thr Trp Asn Thr Gln Thr Arg
             100                   105                   110

Leu Glu Arg Val Asp Lys Pro Ile Ser Arg Asp Val Arg Ser Gln Asn
         115                   120                   125

Ile Lys Gly Asp Ala Ser Val Arg Lys Asn Lys Ile Pro Leu Pro Pro
 130                   135                   140

Pro Arg Pro Leu Ile Thr Leu Pro Lys Lys Tyr Gln Pro Leu Pro Pro
145                   150                   155                   160

Glu Pro Glu Ser Ser Arg Pro Pro Leu Ser Gln Arg His Thr Phe Pro
                 165                   170                   175

Glu Val Gln Gly Met Pro Ser Gln Ile Ser Leu Arg Asp Leu Ser Glu
             180                   185                   190

Val Leu Glu Ala Glu Lys Val Pro His Asn Gln Arg Lys Pro Glu Ser
         195                   200                   205

Thr His Leu Leu Glu Asn Gln Asn Thr Gln Glu Ile Pro Leu Ala Ile
     210                   215                   220

Ser Ser Ser Ser Phe Thr Thr Ser Asn His Ser Val Gln Asn Arg Asp
225                   230                   235                   240

His Arg Gly Gly Met Gln Pro Cys Ser Pro Gln Arg Cys Gln Pro Pro
                 245                   250                   255

Ala Ser Cys Ser Pro His Glu Asn Ile Leu Pro Tyr Lys Tyr Thr Ser
             260                   265                   270

Trp Arg Pro Pro Phe Pro Lys Arg Ser Asp Arg Lys Asp Val Gln His
         275                   280                   285

Asn Glu Trp Tyr Ile Gly Glu Tyr Ser Arg Gln Ala Val Glu Glu Ala
 290                   295                   300

Phe Met Lys Glu Asn Lys Asp Gly Ser Phe Leu Val Arg Asp Cys Ser
305                   310                   315                   320

Thr Lys Ser Lys Glu Glu Pro Tyr Val Leu Ala Val Phe Tyr Glu Asn
                 325                   330                   335

Lys Val Tyr Asn Val Lys Ile Arg Phe Leu Glu Arg Asn Gln Gln Phe
             340                   345                   350

Ala Leu Gly Thr Gly Leu Arg Gly Asp Glu Lys Phe Asp Ser Val Glu
         355                   360                   365

Asp Ile Ile Glu His Tyr Lys Asn
     370                   375
```

US 6,831,151 B1

MAST CELL-SPECIFIC SIGNAL TRANSDUCING MOLECULES AND CDNAS THEREOF

This application is a U.S. national stage of International Application No. PCT/JP00/06351 filed Sep. 18, 2000.

TECHNICAL FIELD

The present invention relates to a signal transducer specifically expressed in mouse and human mast cell, and polynucleotides (cDNAs) encoding this protein molecule. More particularly, the present invention relates to a novel protein that is useful, for example, as a target molecule far screening a therapeutic agent for allergic diseases, and various genetic engineering materials useful for production and functional analysis of this protein.

BACKGROUND ART

The type-I allergic response is a complicated immune reaction induced by release of granules containing histamine and serotonin through cross-linking of high affinity IgE receptors mainly expressed in the mast cell and basophilic leukocytes with IgE antibodies and allergens. This reaction has been elucidated to be composed of the following three stages:

A) An initial stage including production of cytokines such as IL-4 and IL-5 from T cell by stimulation of allergens, production of the IgE antibody from B cell, and differentiation and proliferation of the mast cells induced by production of the cytokines;

B) An intermediate stage from cross-linking of Fcε receptors by the IgE antibody and allergen to degranulation of the mast cell; and C) A later stage such as enhanced vascular permeability by histamine and serotonin after degranulation.

The inventors of the present invention have isolated an adapter molecule BASH that is specifically expressed in B cell (J. Immunol, 161:5804–5808, 1998). This BASH has a similar molecular structure to SLP-76 (J. Biol. Chem., 270:7029–7032, 1995) that is expressed in T cell, and indicates the presence of a family of signal transducers specific to hemopoietic immunoreceptors through structural and functional analysis.

While suppression of IgE antibody production (Primary Stage) by B cell using a hyposentitization therapy, or suppression of the later stage by administration of anti-histaminic agent have been used today for treating allergies, neither of them serves as an effective therapy in the current situations.

A part or the molecular mechanism of the type-I allergy response is being made clear, on the other hand, as described above. However, the signal transduction mechanism involved in degranulation of mast cell through the high affinity IgE receptor has not been known yet. It is inevitable to elucidate the molecule involved in the degranulation process of mast cell not only for elucidating the molecular mechanism of the allergy response but also for developing therapeutic methods or therapeutic agents of the allergic diseases. Particularly, since the mast cell plays a critical role in expression of the allergic conditions, the signal transducer that is specifically expressed in mast cell is quite important for developing novel antiallergic agents that selectively block the FCε receptor signal transduction system that causes the degranulation reaction involving release of histamine and serotonin.

The object of the present invention performed based on the foregoing situations is to provide signal transducers specifically expressed in mouse and human mast cells, and polynucleotides (cDNAs) encoding these protein molecules.

Another object of the present invention is to provide various genetic engineering materials involved in the signal transducers.

DISCLOSURE OF INVENTION

For solving the problems above, the present invention provides the following inventions (1) to (10).

(1) A signal transducer specifically expressed in mouse mast cells, which is a purified protein having the amino acid sequence of SEQ ID No. 2.

(2) A signal transducer specifically expressed in human mast cells, which is a purified protein having the amino acid sequence of SEQ ID No. 4.

(3) A polynucleotide consisting of the base sequence of SEQ ID No. 1, which encodes the protein of (1).

(4) A polynucleotide having the base sequence of SEQ ID No. 3, which encodes the protein of (4).

(5) An expression vector involving the polynucleotide of (3).

(6) An expression vector involving the polynucleotide of (4).

(7) A cell transformed with the expression vector of (5), which produces the protein of (6).

(8). A cell transformed with the expression vector of (6), which produces the protein of (2).

(9) An antibody against the protein of (1).

(10) An antibody against the protein of (2).

BEST MODE FOR CARRYING OUT THE INVENTION

Figure 1:
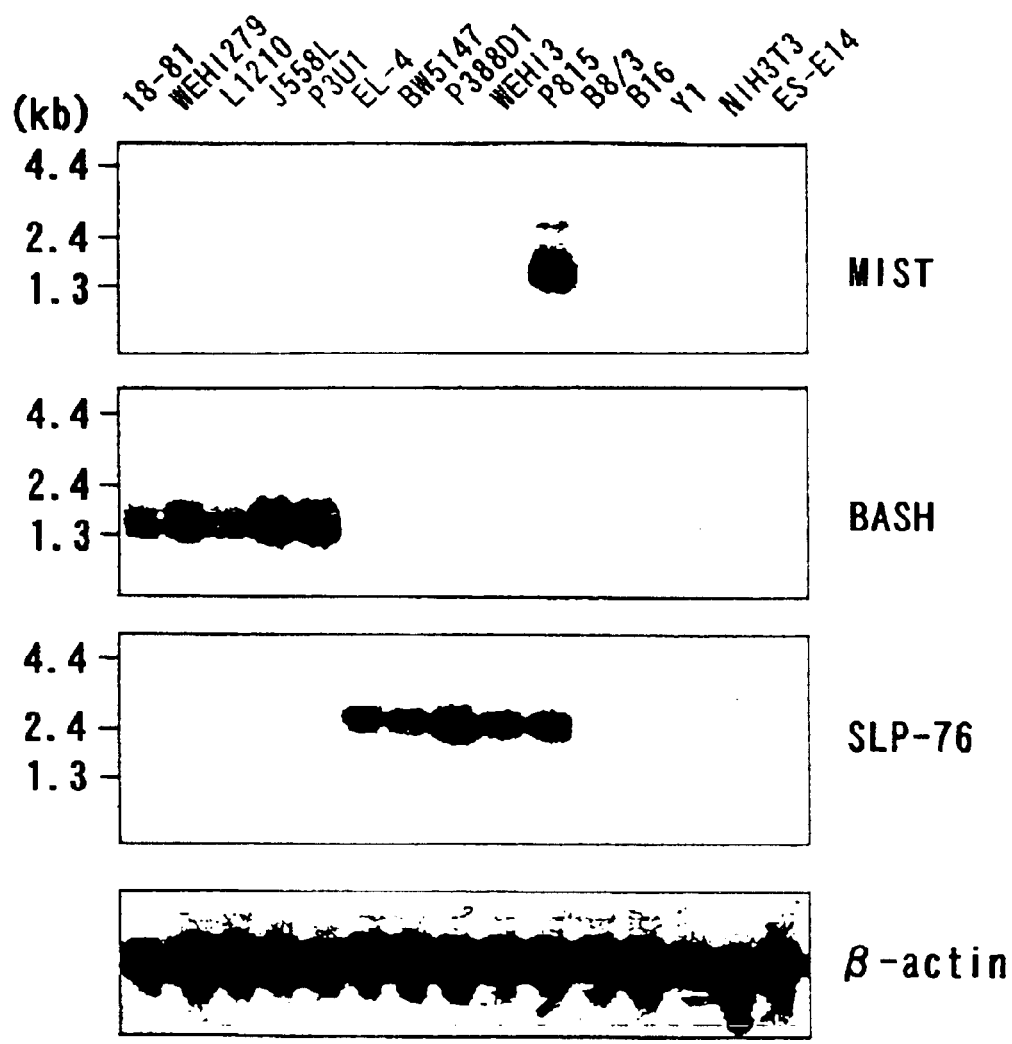
FIG. 1 shows the results of Northern blot analysis investigating expression of MIST, BASH and SLP-76 in the hemopoietic and non-hemopoietic cell lines. 18—18: B-precursor cells, WEH11279; B cells, L1210: B-lymphocyte precursor cells, J558L and P3U1: plasma cells, EL-4 and BW5147: T cells, P388D1 and WEH13: macrophages, P815: mast cell, B8/3: erythroblast, and B16, Y1, NIH3T3 and ES-E14: non-hemopoirtic cell lines.

By screening the expression sequence tag (EST) database, the present inventor identified an EST clone from 13.5 day mouse embryo cDNA library (GenBank accession No. AA166259) which showed a significant amino acid homology to the SH2 domain of chicken BASH (J. Immunol. 161:5804–5808, 1998). The inventor further found that the 1.8 kb mRNA of this clone is not expressed in other hemopoietic cell lines and non-hemopoietic cell lines (such as B cell, T cell and macrophages) in which BASH and SLP-76 are expressed, and is expressed only in mastcytoma cell line P815 (FIG. 1) The expressed protein molecule was named as MIST (Mast Cell-specific Immunoreceptor Signal Transducer) form such specific expression pattern and its function to be described hereinafter.

Embodiments of the present invention will be described in detail hereinafter.

The MISTs according to the inventions (1) and (2) are proteins that are specifically expressed in mouse and human mast cells. The mouse MIST in the invention (1) is a protein encoded in the polynucleotide (full-length cDNA: SEQ ID No. 1) of the invention (3). The human MIST in the invention (2) is, on the other hand, a protein encoded in the polynucleotide of the invention (4) containing the sequence of SEQ ID No. 3 (a partial cDNA).

While the mouse MIST in the invention (1) and human MIST in the invention (2) may be obtained by a method for isolating from organs and cell lines of mouse and human, respectively, by a method for preparing a peptide by a chemical synthesis based on the amino acid sequences provided by the present invention, or by a production method using a recombinant DNA technology using the polynucleotides of the inventions (3) and (4), the recombinant DNA method is preferably used. For example, RNA is prepared by in vitro transcription from a vector having the polynucleotides of the inventions (3) and (4), and MIST is expressed in vitro by in vitro translation using the RNA as a template. The mouse MIST and human MIST encoded by the polynucleotide can be expressed in large scale in prokaryotic cells such as *E. coli* and *Bacillus subtilis*, and in eukaryotic cells such as yeast, insect cells, mammal cells and plant cells by recombination of the coding region with the expression vector using a conventional method.

The polynucleotide (SEQ ID No. 1) of the invention (3) can be obtained by a chemical synthesis or screening of the mouse cDNA library. For cloning the desired polynucleotide from a cDNA library, an oligonucleotide is synthesized based on the base sequence in an arbitrary portion of SEQ ID No. 1, and the polynucleotide is screened by colony or plaque hybridization by the method known in the art using the oligonucleotide as a probe. Alternatively, oligonucleotides that can hybridize to both ends of the desired polynucleotide are synthesized, and the polynucleotide of the invention (3) is prepared by a PCR method using the oligonucleotide as primers and genomic DNA isolated from the mouse cells as a template.

The polynucleotide of the invention (4) can be prepared by isolating a full-length cDNA by hybridization screening or PCR using the oligonucleotides synthesized based on the base sequence at an arbitrary portion of SEQ ID No. 3.

For producing the MIST by expressing the polynucleotide in vitro translation, for example, the polynucleotide of the invention (3) or (4) is recombined into a vector having a RNA polymerase promoter [the inventions (5) and (6)], and the recombinant vector is added to an in vitro translation system such as a lysate of rabbit reticulocytes or wheat germ extract containing the RNA polymerase corresponding to the promoter, thereby producing the mouse and human MIST in vitro. Examples of the RNA polymerase promoters include T7, T3 and SP6. Examples of the vectors containing the RNA polymerase are pKA1, pCDM8, pT3/T7 18, pT7/3 19 and pBluescript II.

For producing the MIST by expressing the polynucleotide in microorganisms such as *E. coli*, an expression vector [the invention (5) and (6)] is prepared by recombining the polynucleotide of the invention (3) or (4) into an expression vector having an origin capable of replication in microorganisms, a promoter, a ribosome binding site, DNA cloning sites and terminator. After transforming host cell with this expression vector, the transformant obtained [the inventions (7) and (8)] is cultured for large scale production of MIST encoded by these polynucleotides in microorganisms. MIST fragments containing arbitrary regions may be obtained by adding an initiation codon and a termination codon before and after the arbitrary coding region. Or, the protein can be expressed as a fusion protein with other proteins. Only the protein regions encoded by this cDNA may be obtained by cleaving the fusion protein with an appropriate protease. Examples of the expression vector for use in *E. coli* include a pUC series vector, pBluescript II, pET expression system and pGEX expression system.

For producing the MIST by expressing the polynucleotide in eukaryotic cell, the polynucleotide of the invention (3) or (4) is recombined with an expression vector for eukaryotic cells that comprises a promoter, splicing site, poly(A) additional site to prepare a recombinant vector [the inventions (5) and (6)], and the vector is introduced into the eukaryotic cell to transform a host cell [the inventions (7) and (8)]. Examples of the expression vectors include pKA1, pCDM8, pSVK3, pMSG, pSVL, pBk-CMV, pBK-RSV, EBV vector, pRS and pYES2. MIST may be expressed as a fusion protein to which various tags such as His tag, FLAG tag and GFP by using pIND/V5-His, pPLAG-CMV-2, pEGFP-N1 and pEGFP-C1 as an expression vector. While cultured cells of a mammal such as monkey kidney cells COS7 and Chinese hamster ovary cells CHO, budding yeast, dividing yeast, silkworm cells and African clawed frog egg cells are usually used as the eukaryotic cells, any eukaryotic cells may be used so long as they are able to express MIST. The expression vector can be introduced into the eukaryotic cell by a conventional method such as an electroporation method, a calcium phosphate method, a liposome method, and a DEAE dextran method.

A combination of separation methods known in the art may be used for purifying the desired protein from the culture after allowing MIST to express in the prokaryotic cells and eukaryotic cells. For example, these methods include treatment with a denaturation reagent such as urea or with a surface active agent, ultrasonic treatment, enzymatic digestion, salting-out and solvent precipitation method, dialysis, centrifugation, ultrafiltration, gel filtration, SDS-PAGE, isoelectric focusing electrophoresis, ion exchange chromatography, hydrophobic chromatography, affinity chromatography and reversed phase chromatography.

The mouse MIST of the invention (1) and the human MIST of the invention (2) contain any peptide fragments (five amino acid residues or amore) represented by SEQ ID Nos. 2 and 4. These peptide fragments may be used for preparing antibodies. The MISTs of the inventions (1) and (2) are modified in any ways in the cell after translation. Accordingly, these modified proteins are also included within the scope of the present invention. Examples of modification after translation include elimination of N-terminal methionine, N-terminal acetylation, addition of sugar chains, restricted degradation by an intracellular protease, addition of miristoleic acid, isoprenylation and phosphorylation.

Polymorphism by individual differences is often observed in the animal gene. Accordingly, polynucleotides having addition or deletion of one or plural nucleotides and/or substitution with other nucleotides in the base sequence of SEQ ID Nos. 1 and 3 are also included within the scope of the present invention.

Likewise, MISTs having addition or deletion of one or plural amino acids and/or substitution with other amino acids caused by the alteration of polynucleotides as described above are also included within the scope of the present invention so long as it has an activity of the MIST containing the amino acid sequences of SEQ ID Nos. 2 and 4.

The polynucleotides in the inventions (3) and (4) also include DNA fragments (10 bp or more) comprising any partial base sequence of SEQ ID Nos. 1 and 3. DNA fragments comprising sense strand and antisense strans are also included within the scope as described above.

The antibodies according to the inventions (9) and (10) can be obtained from serums of an animals immunized with the proteins of the inventions (1) and (2). Chemically synthesized peptides based on the amino acid sequences of SEQ ID Nos. 2 and 4, and MIST itself expressed in the eukaryotic or prokaryotic cells may be used for the antigen.

Otherwise, the antibodies may be produced from collected serums after introducing the expression vector for the eukaryotic cell into the muscle or skin of an animal by injection or using a gene gun (for example, the method described in Japanese Patent Publication No. 7-31387). The animals used include mouse, rat, rabbit, goat and chicken. Monoclonal antibodies against MIST can be obtained by preparing a hybridoma by fusing B cell extracted from an immunized animal with myeloma cells.

EXAMPLES

The present invention is described in more detail with Examples, the present invention is not restricted in any sense by the Examples as set forth below.

Example 1 cDNA Cloning

Full-length mouse MIST cDNA was isolated from PT18 cDNA library with 5'- and 3'-RACE (Marathon cDNA amplification kit, made by Clontech Co.), using primers prepared based on the sequence information of EST clone (GenGank accession No. AA166259). The partial cDNA of human MIST was amplified by PCR using mRNA prepared from human cord blood mast cell (HCMC) cultured with IL-6 and the stem cell factor (SFC: Peprotech) according to the method in "Blood 86:3705–3714, 1995.

The sequence of the cDNA obtained was determined by the method known in the art, confirming that the mouse MIST cDNA comprises the base sequence represented by SEQ ID No. 1 and the human MIST partial cDNA comprises the base sequence represented by SEQ ID No. 3. It was also confirmed that the mouse MIST has the amino acid sequence represented by SEQ ID No. 2 with a molecular weight of about 60 kDa. Eight Tyr residues capable of phosphorylation are found in the mouse MIST from the N-terminus to the central part. The C-terminal part contains an SH2 domain which is most similar to the SH2 domain of mouse BASH and SLP-76 in amino acid level (41% and 53% identities, respectively). In addition, the central part of MIST is rich in Pro residues, and contains SH3 domain-binding motif. Consequently, MIST was confirmed to have the features as a signal molecule.

The human MIST showed, on the other hand, 60% homology with the mouse MIST in the amino acid level.

Example 2

Construction of Expression Vector

The coding region of the mouse MIST cDNA obtained in Example 1 was amplified by PCR, and the amplified region was inserted between the EcoRI and Sal I sites of pCATneo expression vector (J. Immunol., 161:5804–5808, 1998) to construct a recombinant expression vector (pCATneo-MIST-WT).

The MIST mutant (MIST-YF) in which amino acids (Tyr) at 69, 96, 101, 153, 174 and 188 in SEQ ID No. 2 were substituted with other amino acids (Phe) was prepared by a PCR-based mutagenesis using a commercially available mutation kit (made by Stratagene Co.), and subcloned the MIST-YF into the pCATneo to construct a recombinant expression vector (pCATneo-MIST-YF).

Example 3

Preparation of Transformed Cells

The rat must cell line RBL-2H3 were transfected with the recombinant expression vectors pCATneo-MIST or pCATneo-MIST-YF prepared in Example 2 to prepare the transformed cell RBL-2H3-MIST and RBL-2H3-MIST-YE.

Example 4

Preparation of Antibody

An anti-MIST antibody was prepared from a rabbit immunized with a fusion protein of a polypeptide comprising the amino acid sequence 193–435 in SEQ ID No. 2 and glutathione-S-transferase (GST). The antisera were at first precleared with Seharose beads coupled with GST alone, and then purified with an affinity column coupled with GST-MIST fusion protein. Specificity of the antibody purified with affinity chromatography was confirmed by an immunoblot analysis on cell lysates from COS cells transfected with mouse MIST cDNA.

Example 5

Confirmation of MIST Expression in Various Cell Lines

Expression of the mouse and human MISTs obtained in Example 1 was confirmed by RT-PCR. The objective cells were IL-3-induced mouse bone marrow-derived mast cells (BMMC), mouse mast cell line PT18, human mast cells (HCNC) cultured with SCF and IL-6, and other hemocyte cell lines (Jurkat: human T cell, Romas: human B cell, KU812: human basophil precursor cell, EOL-1: human eosinophil precursor cell).

Figure 2:
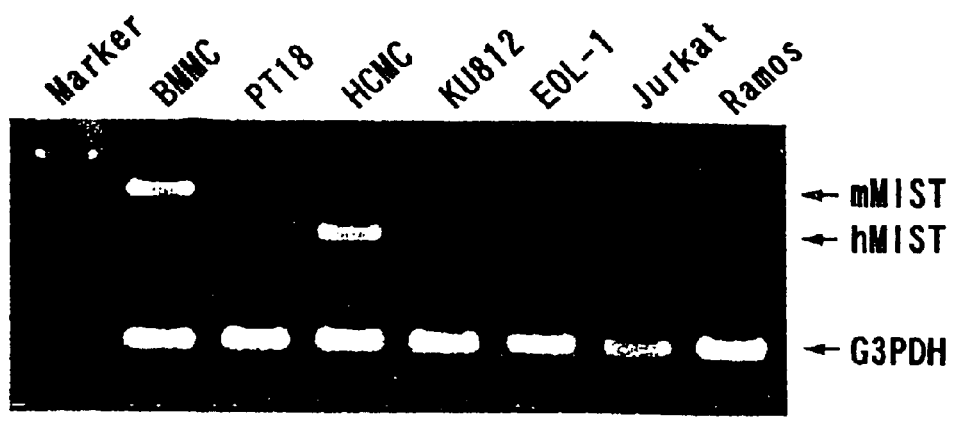
FIG. 2 shows the results of RT-PCR analysis investigating expression of MIST in various hemopoietic cell lines.

The results are as shown in FIG. 2. Although expression of MIST was found in mast cells BMMC, PT18 and HCNC, other cell lines showed no expression.

Figure 3:
FIGS. 3 and 4 show the results of immunohistological analysis investigating expression of MIST in inflammatory mast cell in atopic dermatitis of the NC/Nga mouse.
Figure 4:
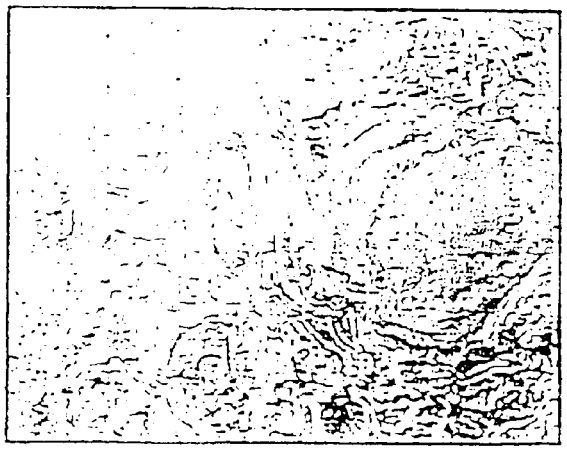

By using the anti-MIST antibody prepared in Example 4, serial tissue sections of NC/Nga mice, which spontaneously develop atopic dermatitis (J. Imunol., 9:461–466, 1997) were stained to clarify whether MIST protein is expressed in normal mast cells in in vivo. The results are shown in FIGS. 3 and 4. Expression of MIST was observed in the inflammatory mast cells in the mouse.

It was confirmed from the results as described above that MIST is a protein specifically expressed in mast cell.

Example 6

Confirmation of Phosphorylation of Tyrosine in MIST

Phosphorylation of tyrosine in MIST by stimulating with FcεRI was investigated using the rat mast cell line RBL-2H3 in which signal transduction of FcεRI had been confirmed.

The transformed cell RBL-2H3-MIST prepared in Example 3 was cultured with 10 μg of anti-DNP mouse IgE (made by Sigma Co.) for 1 hour, and the cells were stimulated with 100 ng/ml of DNP-HSA. The cells were lysed with 1% NP40 lysis buffer, and the lysate was subjected to immune precipitation together with various antibodies.

Tyrosine of the MIST molecule was phosphorylated by stimulating the Fcε receptor on the mast cell IgE and antigens, and MIST associate with signal molecules such as PLC-γ and Vav. Consequently, the MIST molecule was confirmed to be a signal molecule existing at the downstream of the Fcε receptor. MIST was evidently phosphorylated by Lyn kinase among tyrosine kinases present in the mast cell, showing that the Lyn kinase has an important role for degranulation of the mast cell.

Example 7

Investigation of MIST Function in Degranulation of Mast Cell

The effect of over expression of MIST and mutation type MIST on degranulation of the cells was investigated using the transformed cells, RBL-2H3-MIST and RBL-2H3-MIST-YF prepared in Example 3.

The cells were cultured with 1 μg/ml of anti-DNP mouse IgE overnight, washed twice with PBS, and stimulated with DNP-HSA at 37° C. for 30 minutes. Degranulation was confirmed by measuring release of β-hexosaminidase by the method described in the literature (Int. Immunol., 7:251–258, 19921)

Figure 5:
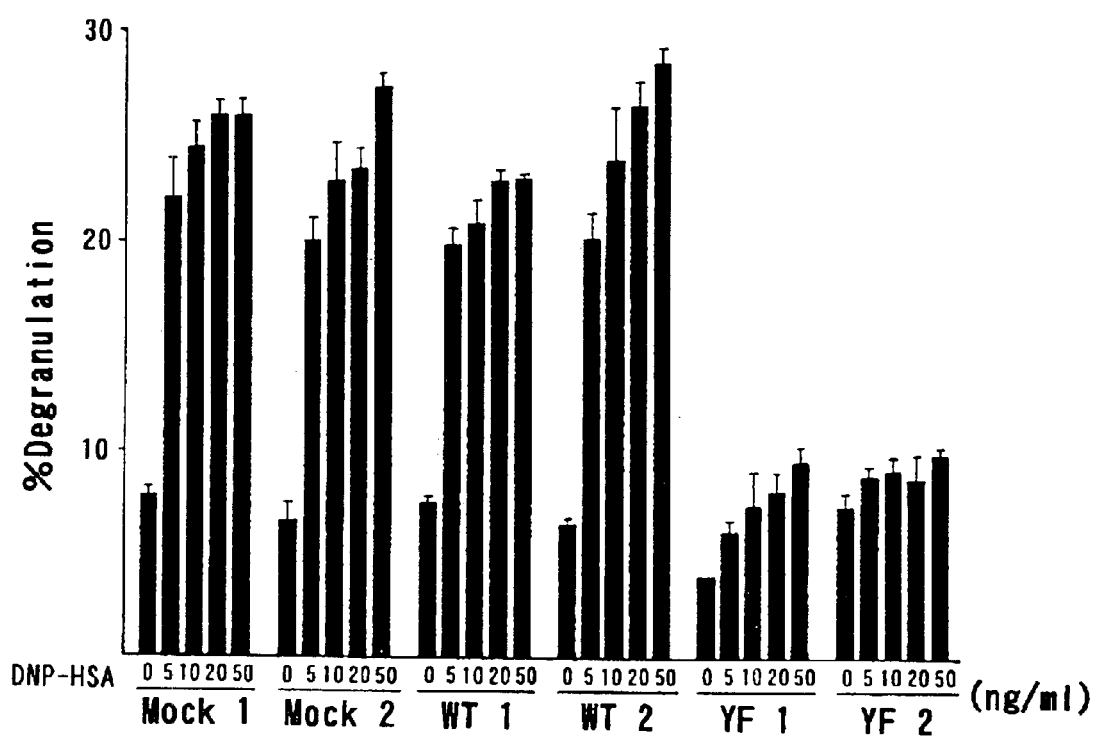
FIG. 5 shows the results of degranulation reaction of RBL-2H3 clone expressing wild-type or mutant MIST.

The results are shown in FIG. 5. Although degranulation of the mast cell was not affected by stimulation with the Fcε receptor when a wild type MIST was over expressed, degranulation of the mast cell via the FCε receptor was significantly suppressed by over expression of the MIST mutant (MIST-YF).

It was confirmed from the results above that the MIST molecule plays an important role in the signal transduction pathway from stimulation by the Fcε receptor through degranulation.

INDUSTRIAL APPLICABILITY

The present invention provides signal transducers that are specifically expressed in mouse and human mast cells, polynucleotides (cDNAs) encoding this protein molecule and various gene engineering materials concerning these signal transducers. Screening of novel agents for allergic diseases becomes possible by using these signal transducers as targets.

What is claimed is:

1. A signal transducer specifically expressed in mouse mast cells, which is a purified protein having the amino acid sequence of SEQ ID No. 2.

2. A signal transducer specifically expressed in mouse mast cells, which is a purified protein encoded by the nucleic acid sequence of SEQ ID No. 1.

* * * * *